United States Patent [19]

Shenoy

[11] 4,060,608

[45] Nov. 29, 1977

[54] SUBSTITUTED HYDROXYMETHYL BENZODIAZEPINES

[75] Inventor: Umakant Devdas Shenoy, London, England

[73] Assignee: DDSA Pharmaceuticals, London, England

[21] Appl. No.: 622,349

[22] Filed: Oct. 14, 1975

Related U.S. Application Data

[63] Continuation-in-part of Ser. No. 487,478, July 11, 1974, abandoned, Continuation-in-part of Ser. No. 481,944, June 21, 1974, abandoned.

[51] Int. Cl.² .................. A61K 31/55; C07D 405/06; C07D 243/20

[52] U.S. Cl. ..................... 424/244; 424/263; 424/285; 260/239 BD; 260/294.8 C; 260/294.9; 260/295 F; 260/296 B; 260/347.2; 260/347.4; 260/347.7

[58] Field of Search ......... 260/347.7, 296 B, 239 BD, 260/294.8 C, 294.9, 295 F, 347.2, 347.4; 424/244, 263, 285

[56] References Cited

PUBLICATIONS

Burmistrov, Chem. Abst., vol. 44, (1950) 1055e.

*Primary Examiner*—Henry R. Jiles
*Assistant Examiner*—Bernard Dentz
*Attorney, Agent, or Firm*—Burgess, Dinklage & Sprung

[57] ABSTRACT

Novel 2-disubstituted amino 3H-1,4-benzodiazepines and their 4-oxides, acid addition salts thereof and a method for their preparation from 2-monosubstituted amino benzodiazepines and their 4-oxides.

9 Claims, No Drawings

SUBSTITUTED HYDROXYMETHYL BENZODIAZEPINES

This is a continuation-in-part of copending application Ser. No. 487,478 filed 1974 July 11 and now abandoned which in turn is a continuation-in-part of Application Ser. No. 481,944 filed 1974 June 21 and now abandoned. Both earlier Applications were filed by Umakant Devdas Shenoy.

BACKGROUND OF THE INVENTION

The invention provides 2-disubstituted amino benzodiazepine derivatives in which one of the substituents on the amino group in the 2-position has a hydroxy group in the α position to the said amino group.

Many 3H-1,4-benzodiazepines are known to have a useful action on the central nervous system and are regularly administered as tranquilizers in the field of human therapy.

SUMMARY OF THE INVENTION

It is an object of the invention to provide novel 3H-1,4-benzodiazepines some of which are of interest in the fields of human and animal therapy and some of which are of interest as intermediates in the synthesis of other useful drugs.

According to the invention there are provided benzodiazepine derivatives of the general formula I

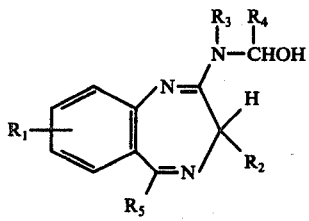

in which $R_1$ represents a radical selected from the group consisting of hydrogen and halogen atoms and trifluoromethyl, cyano, nitro, lower alkyl, lower alkoxy and lower alkylthio groups;

$R_2$ represents a radical selected from the group consisting of hydrogen atoms and hydroxy, lower alkyl, lower alkoxy and lower alkanoyloxy groups;

$R_3$ represents a radical selected from the group consisting of lower alkyl, hydroxy (lower alkyl), lower alkenyl and benzyl groups;

$R_4$ represents a radical selected from the group consisting of lower alkyl and furyl groups; and $R_5$ represents a radical selected from the group consisting of phenyl, (lower alkyl) phenyl, nitrophenyl, halophenyl and pyridyl groups, 4-oxides of the said compounds and acid addition salts of the said compounds and of their 4-oxides with pharmaceutically acceptable acids. The acid addition salts according to the invention may be salts with pharmaceutically acceptable inorganic or organic acids such as hydrochloric acid, hydrobromic acid, nitric acid, sulphuric acid, acetic acid, formic acid, phosphoric acid, perchloric acid, succinic acid, maleic acid, citric acid and fumaric acid.

As used herein the term "halogen" means bromine, chlorine, fluorine or iodine. The term "lower alkyl" refers to both straight-chain and branched-chain alkyl groups containing from 1 to 10 carbon atoms, for example methyl, ethyl, isopropyl, n-butyl, n-amyl and n-hexyl. The term "lower alkenyl" means straight-chain and branched-chain alkenyl groups containing from 2 to 6 carbon atoms, for example vinyl, allyl, butenyl, hexenyl and isobutenyl. The term "lower alkoxy" refers to both straight-chain and branched chain alkoxy groups containing 1 to 6 carbon atoms, for example methoxy, ethoxy and butoxy. The term "lower alkanoyloxy" refers to both straight-chain and branched-chain alkanoyloxy groups containing from 2 to 6 carbon atoms, for example acetoxy, propionyloxy and butyryloxy.

Specifically the compounds of the present invention are useful for their phychotropic action on the central nervous system, for their tranquilizing, sedative and hypnotic properties. In such treatment they are generally employed in a dosage between 1 mg and 10 mg depending on the age and condition of the patient. In larger doses they produce sedation, and when the sedative dose is increased they have hypnotic effects. They can be applied in the form of tablets, capsules, suppositories or syrup, or in injectable form. They can be formulated with adjuvants and excipients as isusual with products of this nature. This invention accordingly provides therapeutic compositions comprising one or more compounds according to the invention in admixture with a pharmacologically acceptable diluent or carrier.

It will be readily appreciated by those skilled in the art that the various substituents that have been found of interest in known compounds with the benzodiazepine nucleus will be equally relevant to the novel compounds of the invention. Examples of preferred identities of $R_1$ are hydrogen, a halogen atom or the trifluoromethyl group at the 7-position, a cyano or nitro group at the 7-position and methyl groups at the 7- and 8-positions. Among these examples, 7-chloro, 7-bromo and 7-nitro are of the greatest interest.

Examples of preferred identities of $R_2$ are hydrogen, hydroxy, methoxy, ethoxy, methyl, ethyl, propyl and acetoxy. Examples of preferred identities of $R_3$ are methyl, ethyl, propyl, allyl, hydroxymethyl and hydroxyethyl. Examples of preferred identities of $R_5$ are phenyl, 2-fluorophenyl and pyridyl.

The compounds in which $R_4$ is furyl are of particular interest. Their psychotropic action is as disclosed above, but in addition their toxicity tends to be low. In particular, the compound 7-chloro-2-(n-methyl-N-1-hydroxy-furfurylamino)-5-phenyl-3H-1,4-benzodiazepine-4-oxide hydrochloride has been shown to have a toxicity, indicated by the $LD_{50}$ for female mice, significantly lower than that of conventional and commercially used benzodiazepine drugs. The 7-day median lethal dose ($LD_{50}$) for female mice was found to be 900 mg/Kg at 23° C and 1080 mg/Kg at 30° C. The higher toxicity at lower temperatures was thought to be caused by hyperthermia induced by the compound under test.

In addition, this compound was found to have minimal diuretic activity at dose levels producing sedation (200 mg/Kg). At a clinical dose level it can therefore be assumed that there would be no diuretic effect.

Of direct importance in connection with the above compound may be the observation of normal neuromuscular coordination in mice at dose levels in mice producing tranquilizing and sedative effects. In humans, this retention of coordination would avoid or reduce the disadvantages of loss of concentration and related side effects commonly associated with benzodiazepine drugs. The observation of this effect was made on groups of five mice subjected to a Rotarod test. Doses of 200 mg/Kg showed marked sedation after 30 minutes and all animals showed difficulty in maintaining balance on the rotating rod. In marked contrast, doses of 20 mg/Kg and 100 mg/Kg had no apparent effect on muscular coordination even though the dose levels produced apparent sedation/tranquillization. The following Table shows the effect of 7-chloro-2-(N-methyl-N-1-hydroxyfurfurylamino)-5-phenyl-3H-1,4-benzodiazepine-4-oxide hydrochloride on the Rotarod performance of groups of 5 mice for 2 minute test periods for 5 hours after dosage.

TABLE

| | Total Number of Falls | | | | |
|---|---|---|---|---|---|
| Time after | Control | SH60 | | | Chlorpromazine |
| dosage (mins.) | - mg./kg. | 20 mg./kg. | 100 mg./kg. | 200 mg./kg. | 15 mg./kg. |
| 0 | 0 | 2 | 2 | 0 | 0 |
| 15 | 0 | 0 | 0 | 0 | 1 |
| 30 | 0 | 0 | 0 | 23 | 0 |
| 45 | 0 | 0 | 0 | 27 | 5 |
| 60 | 0 | 0 | 0 | 36 | 13 |
| 90 | 0 | 0 | 0 | 34 | 17 |
| 120 | 0 | 0 | 0 | 40 | 14 |
| 180 | 0 | 0 | 0 | 26+* | 9 |
| 240 | 0 | 0 | 0 | 37+* | 13 |
| 300 | 0 | 0 | 0 | 30+* | 9 |

*2/5 mice in hypnotic state - not returned to rotarod.

The invention also provides a process for preparing the above compounds which comprises reacting, in acid conditions, a compound of the general formula II

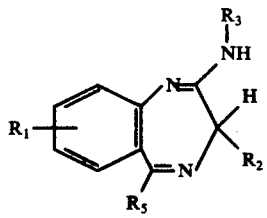

in which $R_1$, $R_2$, $R_3$ and $R_5$ are above defined, or a 4-oxide thereof, with an aldehyde of the general formula

in which $R_4$ is as above defined. Certain suitable starting materials of the general formula II are described and claimed in British Patent Specifications Nos. 864,824 972,969 and 986,903. The molar ratio of starting material of the general formula II to aldehyde is preferably 1:1 to 1:2.

When the aldehyde is acetaldehyde it may, if desired, be generated in situ for example, by the action of the acid in the reaction mixture on paraldehyde.

The reaction is preferably carried out at room temperature (about 20° C) in solution in water, in an organic solvent for the starting materials, for example an aliphatic alcohol containing from 1 to 3 carbon atoms, dioxan or tetrahydrofuran or in a mixture of water and such an organic solvent.

The reaction mixture should be acidic throughout the reaction, which is in marked contrast with the basic conditions previously used when dealing with 2-aminobenzodiazepines. Suitable acids employed to maintain this acidity include hydrochloric acid, hydrobromic acid, nitric acid, sulphuric acid, acetic acid, formic acid, phosphoric acid, perchloric acid, succinic acid, maleic acid, furmaric acid and para-toluene sulphonic acid.

The starting material represented by the formula II can be used in the form of the free base or a suitable acid addition salt. Acid addition salts, for example hydrochloride salts, are preferable, as they are easily soluble in water.

The reaction mixture should be stirred slowly throughout the reaction. Sometimes even at the end of three days, a clear yellowish red solution results without any solid precipitating. Under these circumstances, the reaction product may be extracted with, for example, methylene chloride. Usually the product separates during extraction or stirring with the methylene chloride. If the product does not separate even after this operation, the methylene chloride layer may be separated and diluted with diethyl ether to precipitate the product.

The crude product obtained is usually in the form of an acid addition salt, the nature of which depends on the acidic component used in the reaction.

The following Examples illustrate the invention.

EXAMPLE 1

To a solution of 7-chloro-2-methylamino-5-phenyl-3H-1, 4-benzodiazepine-4-oxide hydrochloride (33.6 g) in water (400 ml) in a 500 ml round-bottomed flask, equipped with a magnetic stirrer, was added concentrated HCl (11 ml) and acetaldehyde (8.25 ml). The flask was stoppered and stirred slowly for 60 hrs. at room temperature (15° to 20° C). The precipitated solid was filtered, washed with water (2×25 ml) pressed well and air dried. It was crystallized from methanol and ether to obtain colourless crystals M.P. 170° to 171° C (with decomposition). The yield was 15 g of 7-chloro-2-[N-methyl-N-(1-hydroxyethyl)]amino-5-phenyl-3H-1,4-benzodiazepine-4-oxide hydrochloride.

Analysis - for $C_{18}H_{19}Cl_2N_3O_2$; calculated C: 56.84, H: 5.00, N: 11.05; found C: 57.46, H: 5.16, N: 11.05.

EXAMPLE 2

Example 1 was repeated using propionaldehyde (10.9 ml) in place of the acetaldehyde. There was obtained 17.1 g of 7-chloro-2-[N-methyl-N-(1-hydroxypropyl)-amino]-5-phenyl-3H-1,4-benzodiazepine-4-oxide hydrochloride. M.P. 194° to 195° C (with decomposition).

Analysis for $C_{19}H_{21}Cl_2N_3O_2$; calculated C: 56.25, H: 5.52, N:10.20; found C: 57.85, H: 5.33, N: 10.68.

EXAMPLE 3

Example 1 was repeated using n-butyraldehyde (13.5 ml) in place of the acetaldehyde. There was obtained 18 g of 7-chloro-2-[N-methyl-N-(1-hydroxybutyl)]amino-5-phenyl-3H-1,4-benzodiazepine-4-oxide hydrochloride. M.P. 199° to 200° C (with decomposition).

Analysis for $C_{20}H_{23}Cl_2N_3O_2$; calculated C: 58.82, H: 5.64, N: 10.29; C: 57.9, H: 5.70, N: 9.94.

EXAMPLE 4

Furfuraldehyde (12 ml) was added to a stirred solution of 7-chloro-2-methylamino-5-phenyl-3H-1,4-benzodiazepine-4-oxide hydrochloride (chlordiazepoxide hydrochloride) (33.6 g) in water (400 ml) and concentrated hydrochloric acid (15 ml) and the reaction mixture was stirred for 60 hours. The resulting precipitate was filtered, washed with water (2 portions of 25 ml each) and air dried. Crystallization at room temperature from a mixture of methanol, diethyl ether and petroleum ether gave 6 g of off-white crystals of 7-chloro-2-(N-methyl-N-1-hydroxyfurfurylamino)-5-phenyl-3H-

1,4-benzodiazepine-4-oxide hydrochloride, melting at 148° C to 150° C with decomposition.

Analysis of the product gave the following results: Calculated for $C_{21}H_{19}Cl_2N_3O_3$: C = 58.3%, H = 4.4%; N = 9.7%; Found: C = 58.4%, H = 4.3%; N = 9.7%.

EXAMPLE 5

Repetition of Example 1 using 7-nitro-2-methylamino-5-phenyl-3H-1,4-benzodiazepine-4-oxide hydrochloride (34.6g) in place of the 7-chloro benzodiazepine compound yields 7-nitro-2-[N-methyl-N-(1-hydroxyethyl)-amino]-5-phenyl-3H-1,4-benzodiazepine-4-oxide hydrochloride.

EXAMPLE 6

Repetition of Example 1 using 7-bromo-2-methylamino-5-phenyl-3H-1,4-benzodiazepine-4-oxide hydrochloride (38.0g) in place of the 7-chloro benzodiazepine compound yields 7-bromo-2-[N-methyl-N-(1-hydroxyethyl)amino]-5-phenyl-3H-1,4-benzodiazepine-4-oxide hydrochloride.

EXAMPLE 7

Repetition of Example 1 using 7-chloro-2-methylamino-5-(2'-fluorophenyl)-3H-1,4-benzodiazepine-4-oxide hydrochloride (35.5g) in place of the 5-phenyl benzodiazepine compound yields 7-chloro-2-[N-methyl-N-(1-hydroxyethyl)-amino]-5-(2'fluorophenyl)-3H-1,4-benzodiazepine-4-oxide hydrochloride.

EXAMPLE 8

Repetition of Example 1 using 7-chloro-2-allylamino-5-phenyl-3H-1,4-benzodiazepine-4-oxide hydrochloride (34.8g) in place of the 2-methylamino benzodiazepine compound yields 7-chloro-2-[N-allyl-N-(1-hydroxyethyl)-amino]-5-phenyl-3H-1,4-benzodiazepine-4-oxide hydrochloride.

EXAMPLE 9

Repetition of Example 1 using 7-chloro-2-(2'-hydroxyethylamino)-5-phenyl-3H-1,4-benzodiazepine-4-oxide hydrochloride (36.6g) in place of the 2-methylamino benzodiazepine compound yields 7-chloro-2-[N-(2'-hydroxyethyl)-N-(1-hydroxyethyl)-amino]-5-phenyl-3H-1,4-benzodiazepine-4-oxide hydrochloride.

EXAMPLE 10

Repetition of Example 1 using 7-chloro-2-methylamino-3-hydroxy-5-phenyl-3H-1,4-benzodiazepine-4-oxide hydrochloride (34.8g) in place of the 3-unsubstituted benzodiazepine compound yields 7-chloro-2-[N-methyl-N-(1-hydroxyethyl)-amino]-3-hydroxy-5-phenyl-3H-1,4-benzodiazepine-4-oxide hydrochloride.

EXAMPLE 11

Repetition of Example 1 using 7-chloro-2-methylamino-3-methoxy-5-phenyl-3H-1,4-benzodiazepine-4-oxide hydrochloride (36.6g) in place of the 3-unsubstituted benzodiazepine compound yields 7-chloro-2-[N-methyl-N-(1-hydroxyethyl)-amino]-3-methoxy-5-phenyl-3H-1,4-benzodiazepine-4-oxide hydrochloride.

EXAMPLE 12

Repetition of Example 1 using 7-chloro-2-methylamino-3-acetoxy-5-phenyl-3H-1,4-benzodiazepine-4-oxide hydrochloride (39.4g) in place of the 3-unsubstituted benzodiazepine compound yields 7-chloro-2-[N-methyl-N-(1-hydroxyethyl)-amino]-3-acetoxy-5-phenyl-3H-1,4-benzodiazepine-4-oxide hydrochloride.

What I claim is:

1. A benzodiazepine derivative of the formula I

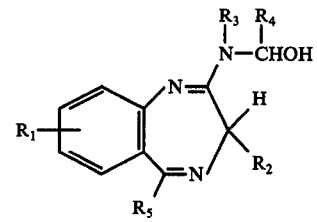

in which $R_1$ represents a radical selected from the group consisting of hydrogen and halogen atoms and trifluoromethyl, cyano, nitro, lower alkyl, lower alkoxy and lower alkylthio:

$R_2$ represents a radical selected from the group consisting of hydrogen atoms and hydroxy, lower alkyl, lower alkoxy and lower alkanoyloxy:

$R_3$ represents a radical selected from the group consisting of lower alkyl, hydroxy (lower alkyl), lower alkenyl and benzyl;

$R_4$ represents a radical selected from the group consisting of lower alkyl and furyl; and $R_5$ represents a radical selected from the group consisting of phenyl, (lower alkyl) phenyl, nitrophenyl, halophenyl, and pyridyl, 4-oxides of the said compounds and acid addition salts of the said compounds and of their 4-oxides with pharmaceutically acceptable acids.

2. 7-chloro-2-[N-methyl-N-(alpha-hydroxyfurfuryl)-amino]-5-phenyl-3H-1,4-benzodiazepine-4-oxide hydrochloride.

3. 7-chloro-2-[N-methyl-N-(1-hydroxyethyl)-amino]-5-phenyl-3H-1,4-benzodiazepine-4-oxide hydrochloride.

4. 7-chloro-2-[N-methyl-N-(1-hydroxypropyl)-amino]-5-phenyl-3H-1,4-benzodiazepine-4-oxide hydrochloride.

5. 7-chloro-2-[N-methyl-N-(1-hydroxybutyl)-amino]-5-phenyl-3H-1,4-benzodiazepine-4-oxide hydrochloride.

6. A process for preparing a derivative according to claim 1, which comprises reacting, in acid conditions, a compound selected from the group consisting of a. compounds of the general formula II

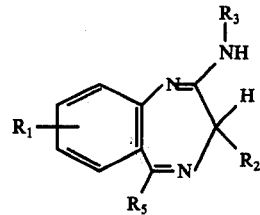

in which $R_1$, $R_2$, $R_3$ and $R_5$ are as defined in claim 1;

b. 4-oxides of the said compounds;

c. acid addition salts of the said compounds; and d. acid addition salts of the said 4-oxides, with an aldehyde of the general formula $R_4$—CHO in which $R_4$ is as defined in claim 1.

7. A process according to claim 6, wherein the molar ratio of the starting material of the general formula II to the aldehyde is from 1:1 to 1:2.

8. A process according to claim 6, carried out at room temperature in solution in a solvent selected from the group consisting of water, an organic solvent for the starting materials and a mixture of water and such an organic solvent.

9. A therapeutic composition comprising a tranquilizing, sedating or hypnosis-inducing amount of at least one compound according to claim 1 in admixture with a pharmacologically acceptable diluent.

* * * * *